US007318434B2

(12) United States Patent
Gumaste et al.

(10) Patent No.: US 7,318,434 B2
(45) Date of Patent: Jan. 15, 2008

(54) SYNTHETIC JET BASED MEDICAMENT DELIVERY METHOD AND APPARATUS

(75) Inventors: Anand V. Gumaste, West Windsor, NJ (US); John Bowers, Clarksburg, NJ (US)

(73) Assignee: Microdose Technologies, Inc., Monmouth Junction, NJ (US)

( * ) Notice: Subject to any disclaimer, the term of this patent is extended or adjusted under 35 U.S.C. 154(b) by 0 days.

(21) Appl. No.: 11/060,267

(22) Filed: Feb. 17, 2005

(65) Prior Publication Data

US 2005/0183724 A1 Aug. 25, 2005

Related U.S. Application Data

(60) Provisional application No. 60/547,323, filed on Feb. 24, 2004.

(51) Int. Cl.
*A61M 16/00* (2006.01)
(52) U.S. Cl. .............................. 128/203.15; 128/203.21
(58) Field of Classification Search ........... 128/200.14, 128/200.16, 203.15, 203.21
See application file for complete search history.

(56) References Cited

U.S. PATENT DOCUMENTS 2,517,482 A 8/1950 Hall
3,507,277 A 4/1970 Altounyan et al.
3,518,992 A 7/1970 Altounyan et al.
3,635,219 A 1/1972 Altounyan et al. ......... 128/266
3,653,380 A * 4/1972 Hansen .................. 128/203.15
3,795,244 A 3/1974 Lax et al. .................. 128/266
3,807,400 A 4/1974 Cocozza ..................... 128/266
3,831,606 A 8/1974 Damani ...................... 128/266
3,948,264 A * 4/1976 Wilke et al. ........... 128/203.15
4,240,418 A * 12/1980 Rosskamp et al. ..... 128/203.15
4,452,239 A * 6/1984 Malem .................. 128/200.17
5,260,321 A * 11/1993 Hof et al. .................... 514/338
5,349,947 A * 9/1994 Newhouse et al. ..... 128/203.21
5,429,302 A * 7/1995 Abbott .................... 239/102.2
5,458,135 A 10/1995 Patton et al. .......... 128/200.14
5,497,763 A * 3/1996 Lloyd et al. ........... 128/200.14
5,694,920 A * 12/1997 Abrams et al. ........ 128/200.16
5,699,649 A * 12/1997 Abrams et al. ............... 53/428
5,724,959 A * 3/1998 McAughey et al. .... 128/203.15
5,740,793 A * 4/1998 Hodson et al. ........ 128/203.15
5,758,823 A 6/1998 Glezer et al. .................. 239/4
5,823,434 A * 10/1998 Cooper .................... 239/102.2
5,894,990 A 4/1999 Glezer et al. ............... 239/423
5,938,118 A * 8/1999 Cooper .................... 239/102.2
6,026,809 A 2/2000 Abrams et al. ........ 128/203.15
6,142,146 A 11/2000 Abrams et al. ........ 128/203.15
6,152,130 A * 11/2000 Abrams et al. ........ 128/204.21
6,328,033 B1 * 12/2001 Avrahami ............. 128/203.15

(Continued)

FOREIGN PATENT DOCUMENTS

WO WO 97/26934 * 7/1997

(Continued)

*Primary Examiner*—Steven O. Douglas
(74) *Attorney, Agent, or Firm*—Hayes Soloway P.C.

(57) ABSTRACT

A dry powder inhaler consisting of first chamber having an orifice for holding a dry powder and a gas, and a second chamber for receiving a deaggregated form of the dry powder and for communicating the deaggregated dry powder to a user. A synthetic jet drives the dry powder from the first chamber to the second chamber.

40 Claims, 10 Drawing Sheets

U.S. PATENT DOCUMENTS

| | | | |
|---|---|---|---|
| 6,347,629 B1 * | 2/2002 | Braithwaite | 128/203.15 |
| 6,457,654 B1 | 10/2002 | Glezer et al. | 239/4 |
| 6,622,720 B2 * | 9/2003 | Hadimioglu | 128/200.16 |
| 6,722,581 B2 | 4/2004 | Saddoughi | 239/102.2 |
| 6,759,159 B1 | 7/2004 | Gray et al. | 429/71 |
| 2003/0041859 A1 * | 3/2003 | Abrams et al. | 128/200.22 |

FOREIGN PATENT DOCUMENTS

| | | | |
|---|---|---|---|
| WO | WO 98/32479 | * | 7/1998 |
| WO | WO 99/64095 | * | 12/1999 |

* cited by examiner

SYNTHETIC JET BASED MEDICAMENT DELIVERY METHOD AND APPARATUS

CROSS REFERENCE TO RELATED APPLICATION

This application claims priority to co-pending U.S. Provisional Application entitled "Synthetic Jet Based Medicament Delivery Method and Apparatus", having Ser. No. 60/547,323, Filed Feb. 24, 2004 which is entirely incorporated herein by reference.

FIELD OF THE INVENTION

The present invention relates generally to the field of metering, packaging and delivery of pharmaceuticals and drugs. Particular utility for the present invention is found in delivery of metered and packaged dry powder medications and drugs for inhalation therapy and will be described in connection with such utility, although other utilities are contemplated, including liquid medication applications.

DISCUSSION OF THE PRIOR ART

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medication in that the drug is deposited exactly at the site desired and where its action may be required; hence, very minute doses of the drug are often equally as efficacious as larger doses administered by other means, with a consequent marked reduction in the incidence of undesired side effects and medication cost. Alternatively, the drug in powdered form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drug is optimum when the drug particles delivered to the respiratory tract are between 1 to 5 microns in size. When the drug particles need to be in this size range the dry powder delivery system needs to address a number of issues:

(1) Small size particles develop an electrostatic charge on themselves during manufacturing and storage. This causes the particles to agglomerate or aggregate, resulting in clusters of particles which have an effective size greater than 5 microns. The probability of these large clusters making it to the deep lungs then decreases. This in turn results in a lower percentage of the drug being available to the patient for absorption.

(2) The amount of active drug that needs to be delivered to the patient may be of the order of tens of micrograms. Since current powder filling equipment cannot effectively deliver aliquots of drugs in microgram quantities with acceptable accuracy, the standard practice is to mix the active drug with a filler or bulking agent such as lactose. This additive also makes the drug "easy to flow". In some cases this filler is sometimes called a carrier. These carrier particles are often larger than the drug particles in size. The ability of the dry powder inhaler to separate drug from the carrier is an important performance parameter in the effectiveness of the design.

(3) Active drug particles with sizes greater than 5 microns will be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bioavailability of the drug.

Prior art dry powder inhalers (DPIs) usually have a means for introducing the drug (active drug plus carrier) into a high velocity air stream. The high velocity air-stream is used as the primary mechanism for breaking up the cluster of micronized particles or separating the drug particles from the carrier. Several inhalation devices useful for dispensing this powder form of medication are known in the prior art. For example, in U.S. Pat. Nos. 3,507,277; 3,518,992; 3,635,219; 3,795,244; and 3,807,400, inhalation devices are disclosed having means for piercing or removing the top of a capsule containing a powdered medication, which upon inhalation is drawn out of the pierced or topped capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced hole and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. No. 5,458,135.

These prior art devices present several problems and possess several disadvantages. For instance, these prior art devices require that the user exert considerable effort in inhalation to effect dispensing or withdrawal of powder from a pierced capsule into the inhaled air stream. With these prior art devices, suction of powder through the pierced holes in the capsule caused by inhalation generally does not withdraw all or even most of the powder out of the capsule, thus causing a waste of the medication. Also, such prior art devices may result in uncontrolled amounts or clumps of powdered material being inhaled into the user's mouth, rather than a constant inhalation of controlled amounts of finely dispersed powder.

The above description of the prior art is taken largely from U.S. Pat. No. 3,948,264 to Wilke et al, who disclose a device for facilitating inhalation of a powdered medication that includes a body portion having primary and secondary air inlet channels and an outlet channel. The secondary inlet channel provides an enclosure for a capsule containing the powdered medication, and the outlet channel is formed as a mouthpiece protruding from the body. A capsule piercing structure is provided, which upon activation forms one or more holes in the capsule so that upon vibration of the capsule by an electromechanical vibrator, the powdered drug may be released from the capsule. The piercing means disclosed in Wilke et al includes three radially mounted, spring-biased piercing needles mounted in a trochoidal chamber. Upon hand rotation of the chamber, simultaneous inward radial motion of the needles pierces the capsule. Further rotation of the chamber allows the needles to be retracted by their spring mountings to their original positions to withdraw the needles from the capsule. The electromechanical vibrator includes, at its innermost end, a vibrating plunger rod which projects into the intersection of the inlet channel and the outlet channel. Connected to the plunger rod is a mechanical solenoid buzzer for energizing the rod to vibrate. The buzzer is powered by a high energy electric cell and is activated by an external button switch. According to Wilke et al, upon inhalation through outlet channel 3 and concurrent pressing of switch 10d to activate the electromechanical vibrating means 10, air is sucked through inlet channels 4 and 12 and the air stream through the secondary inlet channel 4 raises the capsule up against the vibrating plunger rod 10a. The capsule is thus vibrated rapidly with powder being fluidized and dispensed from the pierced holes therein. (This technique is commonly used in manufacturing for dispensing powder through a hopper where the hopper is vibrated to fluidize the powder and move it through the hopper outlet. The pierced holes in the capsule represent the hopper outlet.) The air stream through inlet channel 4 and 12 aids in withdrawal of powder from the capsule and carries this powder through the outlet channel 3 to the mouth of the user. Wilke et al further discloses that the electromechanical vibrator means may be placed at a right angle to the inlet chamber and that the amplitude and frequency of vibration may be altered to regulate dispensing characteristics of the inhaler.

The prior art devices have a number of disadvantages which makes them less than desirable for the delivery of dry powder to the lungs. Some of these disadvantages are:

The performance of the prior art inhalers depends on the flow rate generated by the user. Lower flow rate does not result in the powder being totally deaggregated and hence adversely affects the dose delivered to the patient.

Inconsistency in the bioavailability of the drugs from dose-to-dose because of lack of consistency in the deaggregation process.

Large energy requirements for driving the electromechanical based inhalers which increases the size of the devices making them unsuitable for portable use.

Loss of medication from opened or topped capsules.

Deterioration of medication in open or topped capsules due to exposure to oxygen or moisture.

In my prior U.S. Pat. Nos. 6,026,809 and 6,142,146 (with Abrams), we provide an inhaler that utilizes a vibrator to facilitate suspension of a medication or drug into a gas that overcomes the aforesaid and other disadvantages and drawbacks of the above prior art. More particularly, the inhaler of my aforesaid patent includes a piezoelectric vibrator for deaggregating the medication or drug and driving the deaggregated medication or drug into suspension. In one embodiment of the '809 patent described in FIG. 3, inhaler 10 includes a hard plastic or metal housing 18 having a generally L-shaped longitudinal cross-section. Housing 18 includes four air flow openings 20, 28, 30, and 32. Inhaler 10 includes a main air flow passage 26 which extends the length of the housing 18 from the front 22 (at opening 20) to the rear 24 thereof (at opening 28) and has a generally square-shaped transverse cross-section, so as to permit air flow therethrough (denoted by arrow F in FIG. 1).

Secondary air conduit 31 is generally L-shaped and runs longitudinally from opening 30 in the rear 24 surface of the housing 18 to main passage 26. One-way flow valve 50 is mounted to the inner surface 33 of the main passage 26 via a conventional spring-biased hinge mechanism (not shown), which is adapted to cause the valve 50 to completely block air flow S through the conduit 31 to the main passage 26 when the pressure of the air flow F in the main passage 26 is below a predetermined threshold indicative of inhalation through the passage 26 by a user.

Powder dispensing chamber 51 is formed in housing 18 for holding a capsule 34 containing the powder medication to be inhaled. Housing 18 includes a moveable panel portion 32 in the rear 24 for permitting the capsule 34 to be introduced into the chamber 51 and placed on a seat 52 of vibratory element 36 between guiding means 60A, 60B. Preferably, element 36 comprises a hard plastic or metallic protective shell 37 enclosing a piezoelectric vibrator (not shown). Preferably, the piezoelectric vibrator is mechanically coupled to the drug cartridge 34 so as to permit maximum vibratory energy to be transmitted from the vibrator to the cartridge 34. Guiding means 60A, 60B includes two surfaces which slant downwardly toward the seat 52 so as to permit easy introduction and retention of the capsule on the seat 52 in the chamber 51. Removable panel 32 includes another air inlet 34 for permitting additional air flow S2 from the chamber 51 through conduit 61 into conduit 31 during inhalation by the user. Preferably, panel 32 and housing 18 include conventional mating mounting means (not shown) for permitting the panel 32 to be removably resecurable to the housing by the user between introduction of fresh (i.e., completely full) capsules and removal of spent (i.e., empty) capsules.

The piezoelectric element is made of a material that has a high-frequency, and preferably, ultrasonic resonant vibratory frequency (e.g., about 15 to 50 kHz), and is caused to vibrate with a particular frequency and amplitude depending upon the frequency and/or amplitude of excitation electricity applied to the piezoelectric element. Examples of materials that can be used to comprise the piezoelectric element include quartz and polycrystalline ceramic materials (e.g., barium titanate and lead zirconate titanate). Advantageously, by vibrating the piezoelectric element at ultrasonic frequencies, the noise associated with vibrating the piezoelectric element at lower (i.e., non-ultrasonic) frequencies can be avoided.

In operation a drug-containing package 34 is punctured and inserted onto the surface 52 of vibrator 36 in chamber 51 in the manner described previously. The power switch is placed in the "ON" position and the user inhales air through the conduit 26, air flow F is generated through conduit 26. This causes one-way valve 50 to deflect to admit air flow S through opening 30 into conduit 26, and also causes air flow S2 through opening 34 and chamber 51 into conduit 26. The inhalation of air stream F is sensed by a sensor 40 and is signaled to an actuation controller (not shown), which causes power to be supplied to a controller (not shown). The controller then adjusts the amplitude and frequency of actuating power supplied to the piezoelectric element until they are optimized for the best possible deaggregation and suspension of the powder P from the capsule into the air stream F via air flow S.

In a preferred embodiment of my aforesaid '809 and '146 patents, the medication or drug is supplied from a coiled tape having a plurality of spaced blisters or wells for carrying controlled aliquots of a dry powder medication or drug.

BRIEF DESCRIPTION OF THE INVENTION

The present invention provides a dry powder inhaler which employs synthetic jetting technology to aerosolize drug powder from a blister pack or the like. Synthetic jetting is not new. It was discovered at least as early as 1950 that if one uses a chamber bounded on one end by an acoustic wave generating device and bounded on the other end by a rigid wall with a small orifice, that when acoustic waves are emitted at high enough frequency and amplitude from the generator, a jet of air that emanates from the orifice outward from the chamber can be produced. See, for example, Ingard and Labate, Acoustic Circulation Effects and the Nonlinear Impedance of Orifices, The Journal of the Acoustical Society of America, March 1950. The jet, or so-called "synthetic jet", is comprised of a train of vortical air puffs that are formed at the orifice at the generator's frequency. However, the use of a synthetic jet to deaggregate and eject a dry-powder material from a blister pack or the like in a dry powder inhaler is new, and provides advantages over prior art dry powder inhalers.

More particularly, the present invention provides a dry powder inhaler having a first chamber for and holding a dry powder, and a second chamber connected to the first chamber via a passageway for receiving an aerosolized form of the dry powder from the first chamber and for delivering the aerosolized dry powder to a user. A vibrator is coupled to the dry powder in the first chamber. Since jetting efficiency falls off as the aspect ratio (length to cross-section or diameter) of the passageway, in order to create a synthetic jet the passageway connecting the first chamber to the second chamber preferably, but not necessarily has an aspect ratio equal to at least about one, and the vibrator is energized and coupled to the first chamber so that the distance the gas moves back and forth in the passageway is at least about twice the cross-section or diameter of the passageway.

In one embodiment of the invention, the first chamber is formed in the shape of a cylinder or blister with a vibratory element either forming one wall of the chamber, or the vibratory element is formed apart from the chamber and coupled to the blister.

In a second embodiment the first chamber is formed in the shape of a horn, with a vibratory element either forming one wall of the chamber, or the vibratory element is coupled to a wall of the chamber via a column of gas.

In a third embodiment the first chamber is formed in the shape of a horn, and a standing wave resonator is coupled to a wall of the chamber.

BRIEF DESCRIPTION OF THE DRAWINGS

Other features and advantages of the present invention will be seen from the following detailed description, taken in conjunction with the accompanying drawings, wherein:

FIG. 3a is a cross-sectional view of an enlarged section of the element of FIG. 3;

DETAILED DESCRIPTION OF THE PRESENT INVENTION

Figure 1:
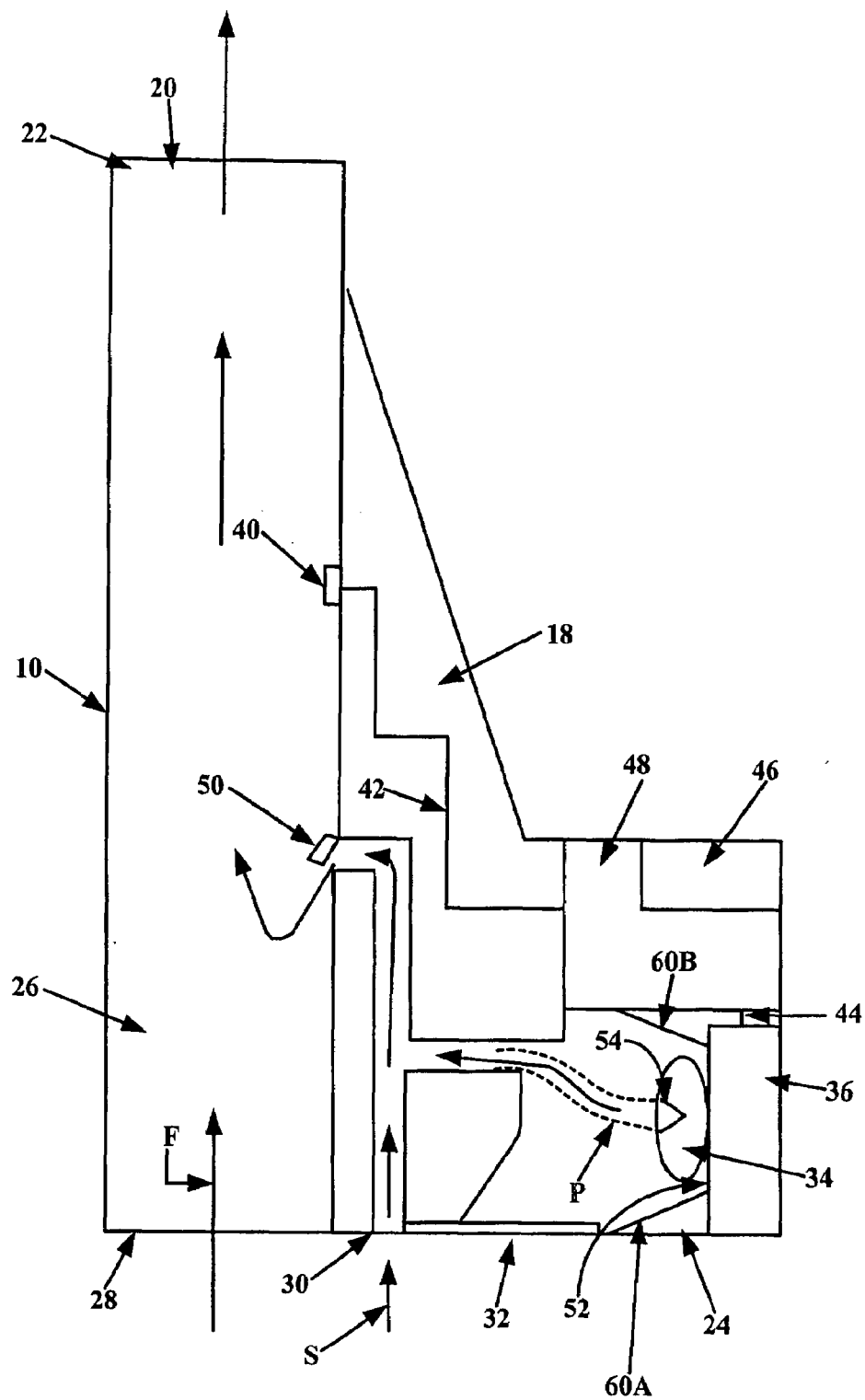
FIG. 1 is a perspective view of one embodiment of the inhaler of the prior art.
Figure 2:
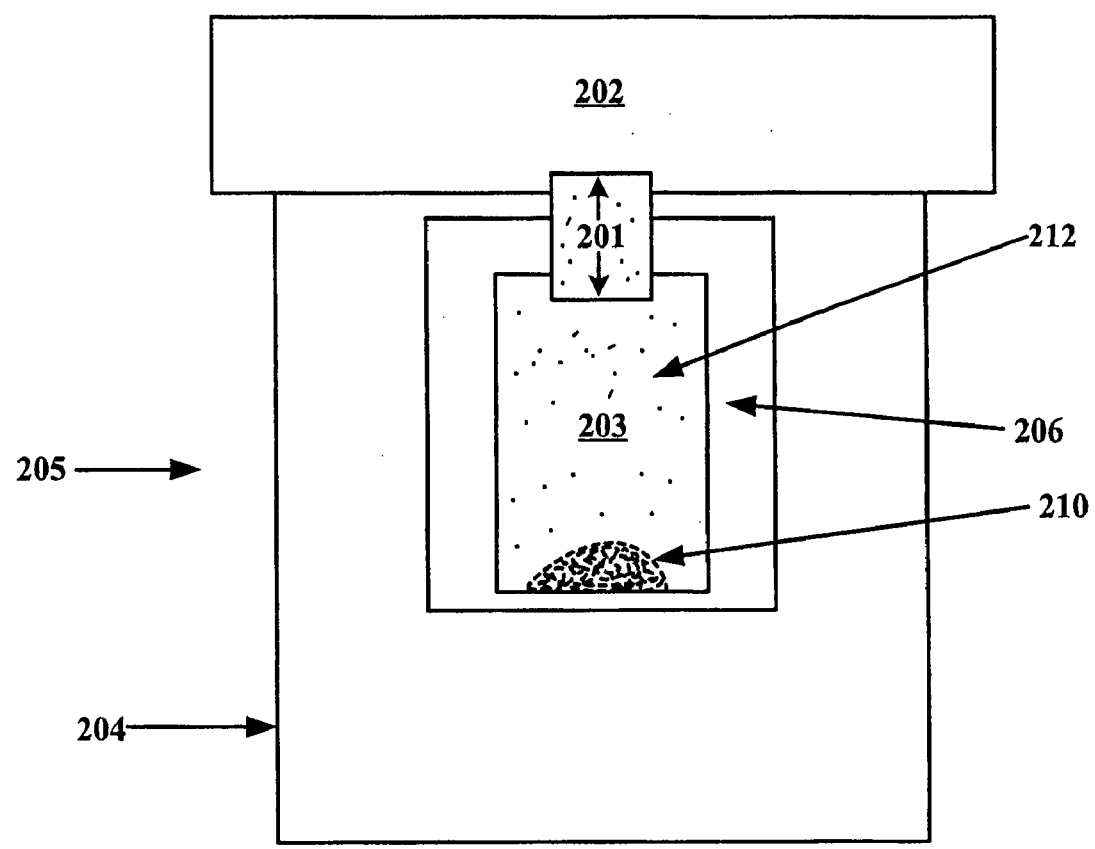
FIG. 2 is a diagram showing the interrelationship between a blister containing a medicament and the synthetic jet of the instant invention.

Referring to FIG. 2, in bare essentials an inhaler 205 in accordance with the present invention comprises a vibrator, e.g., a piezoelectric element 204, a first chamber 203 and a second chamber 202 connected via a passageway 201. The passageway 201 is sized and shaped such that a reciprocating or oscillatory movement of the vibrator coupled to or forming a wall of the first chamber causes the gas in the first chamber to move back and forth through the passageway 201, such that essentially the same mass of gas is moved in each direction, while vortices of the gas are formed at the exits of the passageway 201 such that there is a net flow of gas away from the outlet end of passageway 201, i.e., a synthetic jet of gas is created by the vortices. A vibrator 204, which is operatively connected either directly to the first chamber or via a closed gas tube 206, creates vibrations in the chamber which generate the synthetic jet at the outlet end of passageway 201. The dry powder 210 in the chamber is levitated, at least partially deaggregated into particulate form within the first chamber 203, and suspended in the gas in the chamber to form an aerosol 212. The resulting aerosol is conveyed to the passageway 201 wherein at least a fraction of the suspended dry powder particles passes through the passageway 201 without returning to the first chamber, thereby being communicated between the first chamber 203 and the second chamber 202. The process continues until the majority of the dry powder is evacuated from the first chamber 203.

Although synthetic jets can be formed outside of the bounds of the following parameters, and thus are not excluded from the scope of this invention, the preferred parameters for forming the synthetic jets of this invention are as follows:

1. The aspect ratio of the passageway, i.e., the length to cross-section or diameter of the passageway preferably is at least 0.5 and preferably is greater than or equal to about one. This aspect ratio helps ensure that the mass of gas that moves back and forth in the passageway is created as discrete, well formed slugs of air.
2. The distance the gas moves back and forth through the passageway preferably is greater than about two times the cross-section or diameter of the passageway. This ensures that dry-powder disaggregated by the vortex created has a chance to escape the vortex's presence before the gas moves back through the passageway.
3. The turbulence associated with the vortices and reciprocating gas within the chamber and passageway is minimized to enhance the flow of the synthetic jet. Thus, the surfaces of the passageway and the flange areas around the exits at both ends of passageway 201 preferably will be made free of burrs and other obstructions.
4. The passageway has a cross-section diameter in the range of 0.001" to 0.050".

To ensure the distance that the gas moves back and forth through passageway 201 is greater than about two times the cross-section or diameter of the passageway 201, a minimum power density (or magnitude of pressure change) should be present at the passageway 201. It is possible to generate the minimum power density simply by causing a sufficiently intense vibration in the first chamber 203. Optimally, the first chamber 203 may include a resonator, e.g., a spring-mass or standing-wave resonator, and/or a horn that is used to concentrate energy near the passageway and move the gas between the first chamber and the second chamber.

As will be described below, in a preferred embodiment of the invention, the first chamber 203 and the passageway 201 comprise a pre-formed blister pack containing a dry powder medication or drug.

Figure 3:
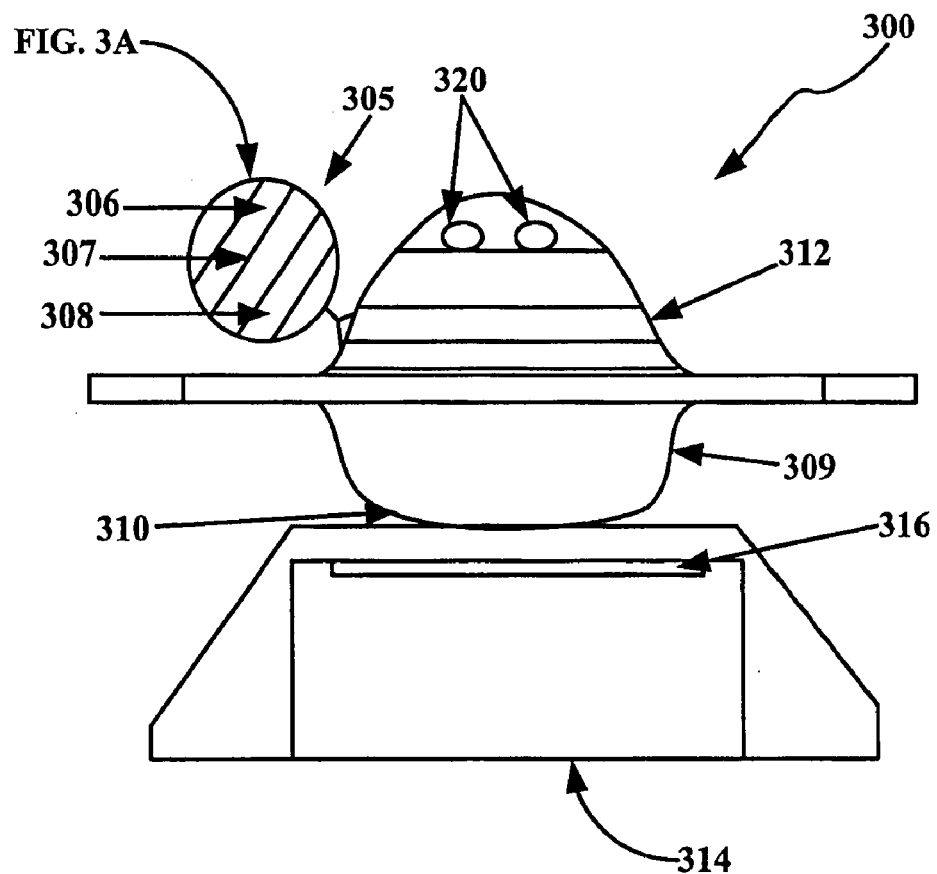
FIG. 3 is a cross-sectional schematic view of a chamber and vibratory element according to a first embodiment of the present invention.
Figure 3B:
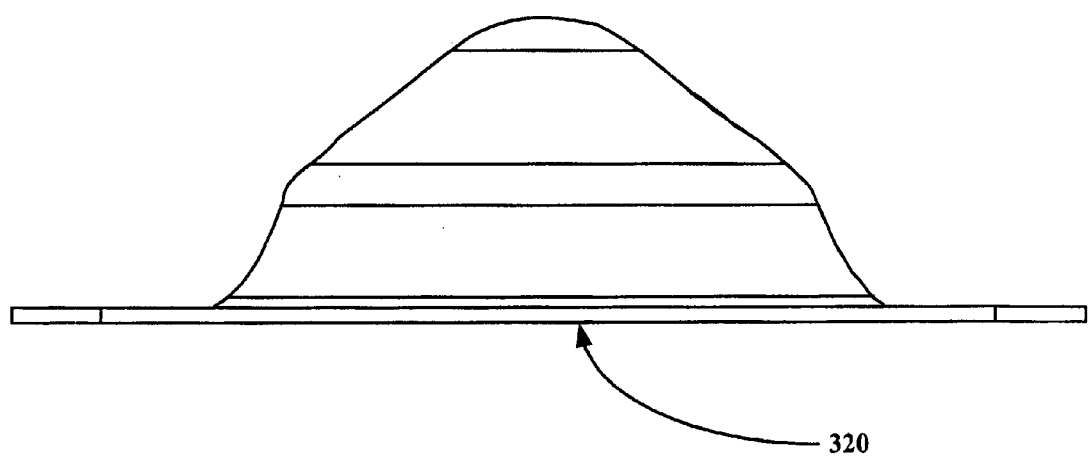
FIG. 3b is a view similar to FIG. 3a of an alternative embodiment of a chamber element made in accordance with the present invention.

Referring to FIGS. 3 and 3a, a blister pack 300 made in accordance with a preferred embodiment of the invention is formed from a tri-laminate material 305 comprising an oriented polyamide sheet 306 on the outside, a middle layer of aluminum foil 307, and polyvinylchloride sheet 308 on the inside. The tri-laminate 305 is about 0.005" thick, and is cold formed into a bowl-shaped base or bottom member 309 having a generally flat bottom 310 of about 0.194" diameter, an overall height of about 0.270" and a diameter at the widest point of about 0.350". Alternatively, the blister pack may be formed with a flat bottom 320 as shown in FIG. 3b. The bottom or base was partially filled with a dry powder, and a top 312, also formed of a tri-laminate was heat sealed to the bottom. Four orifices 320 about 0.01241 diameter were formed in the top of the blister with a spacing of about 0.056" from the axis of the first chamber.

The bottom 310 of the blister pack 300 was placed in contact with a Murata MA40E7S piezoelectric transducer 314 (Murata Electronics North America, Inc., Smyma, Ga.). About 0.006" of the face 316 of the transducer was removed in order to tune the piezo to a resonant frequency of about 34 KHz. The transducer was driven at 34 KHz with a voltage of 150 Vpp. A standing wave resonator was created within the blister. Jets of up to 200 feet per minute were measured with a hot wire anemometer (VWR International catalog #21800-024), thereby producing good evacuation and deaggregation of the dry powder from the blister.

Figure 4:
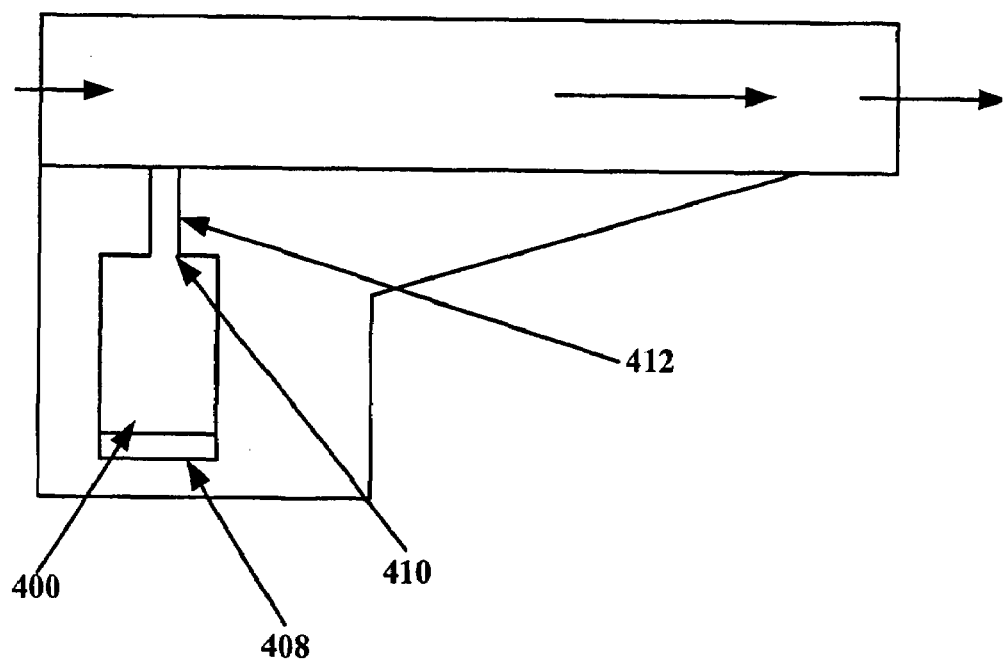
FIG. 4 is a cross-sectional schematic view of a chamber and vibratory element according to a second embodiment of the present invention.

FIG. 4 illustrates a second embodiment of the invention in which acoustic horns are used to move the chamber gas from the first chamber to the second chamber. In the second embodiment, the powder dispensing chamber comprises a cylindrically-shaped first chamber 400 fabricated out of a material such as polycarbonate. A vibratory element 408 is connected to the proximal end of the first chamber 400 thereby causing the magnitude of pressure variations communicated by the vibrator 408 towards the distal end 410 of chamber 400. The resulting pressure variations set up a synthetic jet which dispenses powder from first chamber 400 into the second chamber 404 through passageway 412.

Several experimental cone-shaped horn profiles were machined out of polycarbonate to test the velocity of jets created by a horn-shaped first chamber. In a first example, shown in FIG. 5, the bottom 502 of the horn 504 had a diameter of about 0.400" and was coupled to the vibrating surface 506 of a Murata MA40E7S piezoelectric transducer 508, from which material from the vibrating surface (the face) had been removed such that it had a resonance frequency of 30.4 KHz. The vibrating surface of the transducer thereby formed the bottom wall of the first chamber. The length of the horn, i.e., from its bottom 502 to the top 510 was 0.204". The top end 510 of the horn had a diameter of 0.1". A piece of 0.0125" thick polycarbonate shim stock 512 was adhered to the top of the horn. A orifice 514 of 0.012" diameter was formed in the shim stock such that it was approximately aligned with the axis 516 of the horn. This configuration produced a standing wave resonance at approximately 30 KHz. The transducer was driven at 29.8 KHz at 54 Vpp and a corresponding jet velocity of 1030 feet per minute was measured at the orifice 514. At a higher voltage of 120 Vpp a jet velocity of 1640 feet per minute was measured. In both cases the jet velocity was higher than necessary to achieve good evacuation and deaggregation of the powder from the first chamber.

Figure 6:
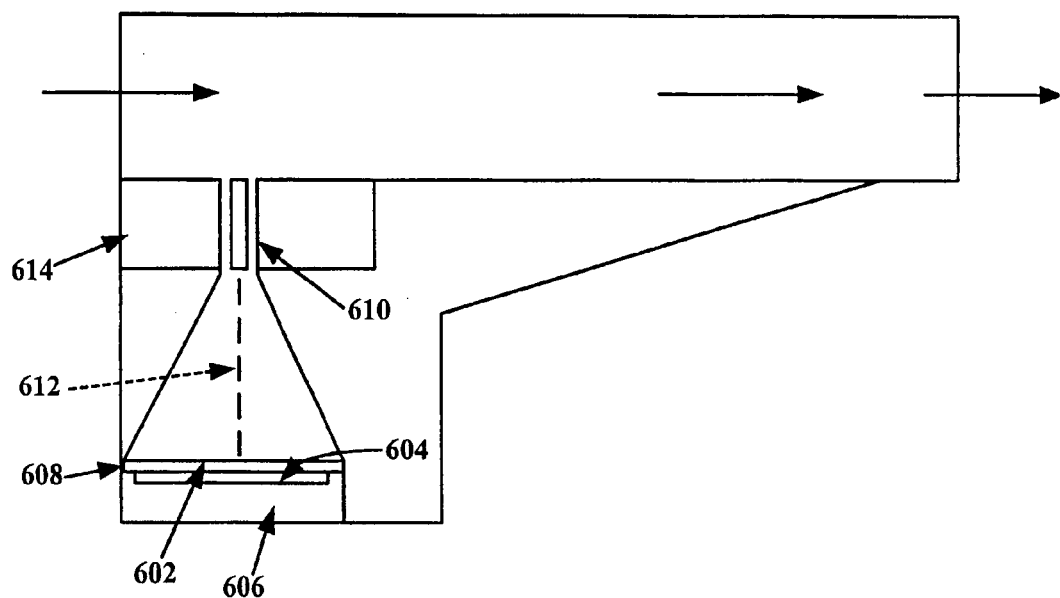
FIGS. 6-9 are views similar to FIG. 5 of further embodiments of the present invention.

Referring to FIG. 6, another cone-shaped horn profile was machined out of aluminum. The bottom 602 of the horn had a diameter of about 0.400" and was coupled to the vibrating surface 604 of a Murata MA40E7S piezoelectric transducer 606, from which material from the vibrating surface (the face) had been removed such that it had a resonance frequency of 30.4 KHz. Interposed between the vibrating surface 604 of the piezoelectric transducer and the horn was a thin laminate film 608 comprising oriented polyamide on the outside, aluminum, and polyvinylchloride on the inside, the film comprising an acoustic window. The tri-laminate was about 0.001" thick and spaced about 0.01" away from the vibrating surface of the piezoelectric transducer. As a result, the vibrations from the transducer were acoustically coupled to the inside of the horn. The distance between the top surface of film 606 and the bottom end of the horn 602 was 0.204". The top end of the horn 602 terminated in a wall 614 which was 0.010" thick and in which were formed 4 orifices 610 each of a diameter of 0.012" with a spacing from the axis 612 of the horn of 0.056". A standing wave resonance frequency of 31.0 KHz was produced. The transducer was driven at 31.0 KHz with a drive voltage of 54 Vpp which produced a jet velocity of 434 feet per minute. When the drive voltage was increased to 120 Vpp the jet velocity increased to 1381 feet per minute. In both cases, the jet velocity is more than adequate to deaggregate and evacuate a dry powder from the chamber.

Figure 7:
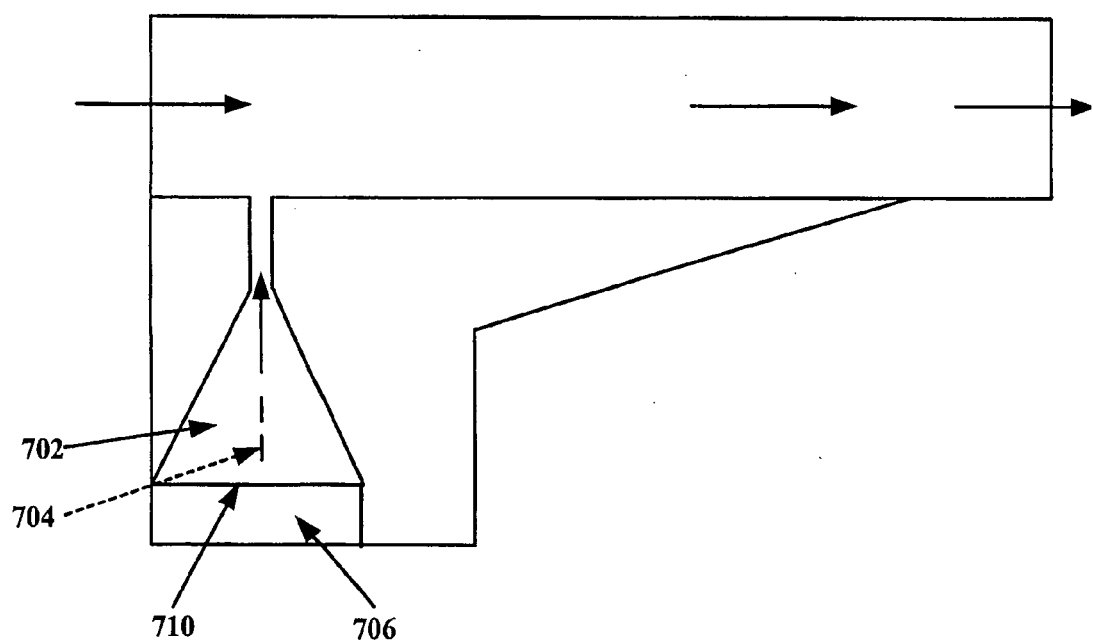

In a third embodiment of the invention, as shown in FIG. 7, a cone shaped first chamber 702 has a horn length (measured along its axis 704) of 0.204". The configuration this provides simultaneously the benefits of a standing wave resonator with the pressure magnitude amplification of a horn to further reduce the magnitude of the pressure variations required of the vibrator to create synthetic jets. In this embodiment, the vibrator 706 is operationally coupled to a flexible wall 710 of the first chamber 702, i.e., as shown in FIG. 7. Alternatively, as shown in FIG. 8, the vibrator 806 may be acoustically coupled to the first chamber 808 through a gas tube 810, to an acoustic window 812, i.e., an area of the first chamber 802 that is sufficiently thin and flexible such that a majority of the vibrational energy will be transferred from one side to the other side of the area. In this embodiment, it is advantageous to minimize the gap between the vibrator 806 and the acoustic window 812 so that the spring constant presented by the medium in the gas tube 812 is of the same order as that presented by the acoustic window 812. Thus, energy losses associated with the use of an acoustic window are minimized.

In a variant of the third embodiment, shown in FIG. 9, a wall 902 of the first chamber 904 may be formed by the vibrator, e.g., by making the wall of a polarized PVDF film, or the like and applying an alternating voltage across the PVDF film so that the PVDF film flexes and generates pressure waves.

Although cylindrical and cone shapes are described above, the chambers may be made in a variety of shapes. In all cases one wall of the chamber should be flat or nearly flat or at least have a generally flattened or slightly rounded surface for interfacing or coupling with the vibratory element.

In each of the above described embodiments, in addition to the vibrators mentioned, the vibratory elements may be a piezoelectric transducer, an electrodynamic (loudspeakers) transducer or a magnetostrictive transducer similar to those that are used in ultrasonic cleaning baths. It also is possible to employ a reciprocating piston pump to generate impulses of gas that can induce synthetic jets. Any vibrator and connection combination suitable for producing the vibrations necessary for generating synthetic jets is within the scope of the invention.

Other configurations are possible and yet are within the scope of the present invention. For example, it may be desirable to place an acoustic window in the chamber to couple the energy from a transducer via a horn to the acoustic window of the chamber. This approach provides two acoustic impedance transformations, one (the horn) which increases the acoustic pressure thereby matching the impedance provided at the acoustic window, and a second (the Helmholtz resonator) that matches the acoustic impedance of the air in the chamber.

Various additional changes may be made in the foregoing without departing from the spirit and scope of the invention, and will be apparent to those skilled in the art.

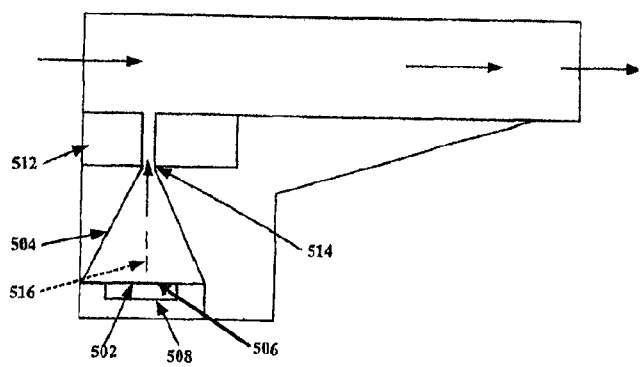

What is claimed is:

1. A dry powder inhaler comprising:
    a first chamber for holding a dry powder and a gas;
    a second chamber directly connected to the first chamber by at least one passageway, formed in a wall of the first chamber, for receiving an aerosolized form of the dry powder from the first chamber and delivering the aerosolized dry powder to a user; and
    a vibrator coupled to the first chamber for aerosolizing the dry powder and cause the aerosolized powder to move back and forth through the passageway whereby to deliver the dry powder from the first chamber to the second chamber as an aerosolized dry powder in the form of a series of fluid vortices, and projected out of the first chamber as a train of discrete slugs of gas containing suspended dry powder, wherein the first chamber has no air inlets other than the passageway connecting the first chamber to the second chamber, and said passageway has an aspect ratio of length to cross-section of at least 0.5.

2. A dry powder inhaler of claim 1, wherein the first chamber is a blister pack containing said dry powder.

3. A dry powder inhaler of claim 1, wherein the first chamber has a cylindrical shape.

4. The dry powder inhaler of claim 1, wherein the first chamber is cone shaped, said cone shape having an apex connecting to a said passageway.

5. The dry powder inhaler of claim 1, wherein said gas comprises air.

6. The dry powder inhaler of claim 1, wherein the first chamber is in the shape of a horn, said horn shape having an apex connected to a said passageway.

7. The dry powder inhaler of claim 1, wherein the distance the slugs of gas and powder moves in either direction is at least twice the diameter of the passageway.

8. The dry powder inhaler of claim 1, wherein the vibrator is a piezoelectric transducer.

9. The dry powder inhaler of claim 1, wherein the passageway has a cross-section diameter in the range of 0.001" to 0.050".

10. The dry powder inhaler of claim 1, wherein the first chamber is constructed of plastic.

11. The dry powder inhaler of claim 1, wherein the first chamber is constructed of metal.

12. The dry powder inhaler of claim 1, wherein the first chamber is constructed of a cold formed laminated material.

13. The dry powder inhaler of claim 12, wherein the laminate material comprises a tri-laminate of oriented polyamide, aluminum foil and polyvinylchloride.

14. The dry powder inhaler of claim 1, wherein the vibrator is coupled to a wall of the first chamber.

15. The dry powder inhaler of claim 1, wherein the vibrator forms at least a part of a wall of the first chamber.

16. The dry powder inhaler of claim 14, wherein the vibrator is coupled to a wall of the first chamber via an acoustic window.

17. A dry powder inhaler comprising:
    a first chamber for holding a dry powder and air;
    said first chamber having at least one orifice formed in a wall of said first chamber each orifice having an aspect ratio of length to cross-section of at least 0.5;
    a vibrator coupled to said first chamber for vibrating said first chamber whereby to cause air in said first chamber to move back and forth through said at least one orifice, whereby to aerosolize said powder in said air, and drive said aerosolized powder and air through said orifice in both directions as a series of fluid vortices of said aerosolized powder and air;
    wherein said powder is expelled from said first chamber to a second chamber through said orifice by synthetic jetting as a train of discrete slugs of air containing said aerosolized powder, wherein said first chamber has no air inlets other than the said at least one orifice.

18. The dry powder inhaler of claim 17, wherein a distance said slugs of said air moves in either direction is at least twice a diameter of the passageway.

19. The dry powder inhaler of claim 17, wherein said chamber is a blister pack containing said dry powder.

20. The dry powder inhaler of claim 17, wherein said chamber includes a standing wave resonator or a Helmholtz resonator.

21. The dry powder inhaler of claim 17, wherein said orifice has a cross-section diameter in the range of 0.001" to 0.050".

22. The dry powder inhaler of claim 17, wherein the vibrator is coupled to a wall of said chamber.

23. The dry powder inhaler of claim 17, wherein the vibrator forms at least a part of a wall of said chamber.

24. The dry powder inhaler of claim 17, wherein the vibrator is coupled to a wall of said chamber via an acoustic window.

25. The dry powder inhaler of claim 17, wherein the vibrator comprises a piezoelectric transducer.

26. A dry powder inhaler comprising:
    a chamber holding a quantity of dry powder and air;
    said chamber having at least one orifice formed in a wall of said chamber, wherein all of the orifices formed in a wall of the chamber have an aspect ratio of length to cross-section of at least 0.5;
    a vibrator coupled to said chamber and tuned to vibrate at a frequency and amplitude to aerosolize said powder in said air and to cause said aerosolized powder to move back and forth in said orifice as a series of fluid vortices, wherein said aerosolized powder is expelled from said chamber, by synthetic jetting, as a series of discrete slugs of air containing said aerosolized dry powder.

27. A dry powder inhaler of claim 26, wherein the first chamber is a blister pack containing said dry powder.

28. A dry powder inhaler of claim 26, wherein the first chamber has a cylindrical shape.

29. The dry powder inhaler of claim 26, wherein the first chamber is cone shaped, said cone shape having an apex connecting to said passageway.

30. The dry powder inhaler of claim 26, wherein the first chamber comprises a standing wave resonator or a Helmholtz resonator.

31. The dry powder inhaler of claim 28, wherein the first chamber is in the shape of a horn, said horn shape having an apex connected to said passageway.

32. The dry powder inhaler of claim 28, wherein the vibrator is a piezoelectric transducer.

33. The dry powder inhaler of claim 28, wherein said orifice has a cross-section diameter in the range of 0.001" to 0.050".

34. The dry powder inhaler of claim 28, wherein the first chamber is constructed of plastic.

35. The dry powder inhaler of claim 28, wherein the first chamber is constructed of metal.

36. The dry powder inhaler of claim 28, wherein the first chamber is constructed of a cold formed laminated material.

37. The dry powder inhaler of claim 36, wherein the laminate material comprises a tri-laminate of oriented polyamide, aluminum foil and polyvinylchloride.

38. The dry powder inhaler of claim 26, wherein the vibrator is coupled to a wall of the first chamber.

39. The dry powder inhaler of claim 26, wherein the vibrator forms at least a part of a wall of the first chamber.

40. The dry powder inhaler of claim 38, wherein the vibrator is coupled to a wall of the first chamber via an acoustic window.

* * * * *

UNITED STATES PATENT AND TRADEMARK OFFICE
CERTIFICATE OF CORRECTION

PATENT NO. : 7,318,434 B2
APPLICATION NO. : 11/060267
DATED : January 15, 2008
INVENTOR(S) : Anand Gumaste et al.

It is certified that error appears in the above-identified patent and that said Letters Patent is hereby corrected as shown below:

The title page, showing an illustrative figure, should be deleted and substitute therefor the attached title page.

Figure 5:
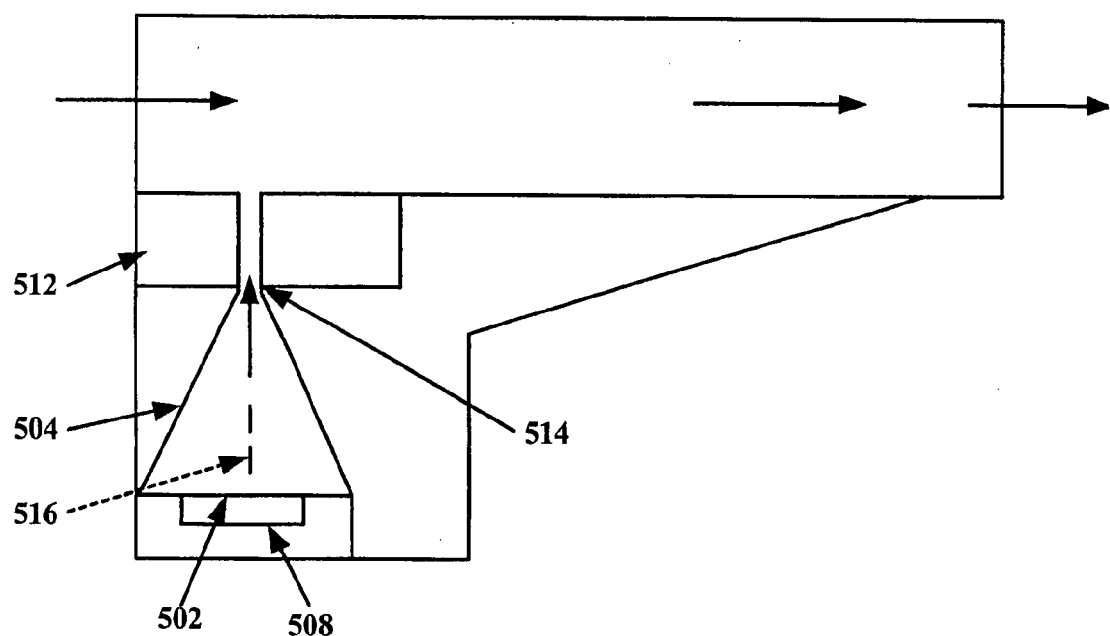
FIG. 5 is a cross-sectional schematic view of a chamber and vibratory element according to a third embodiment of the present invention.
Figure 8:
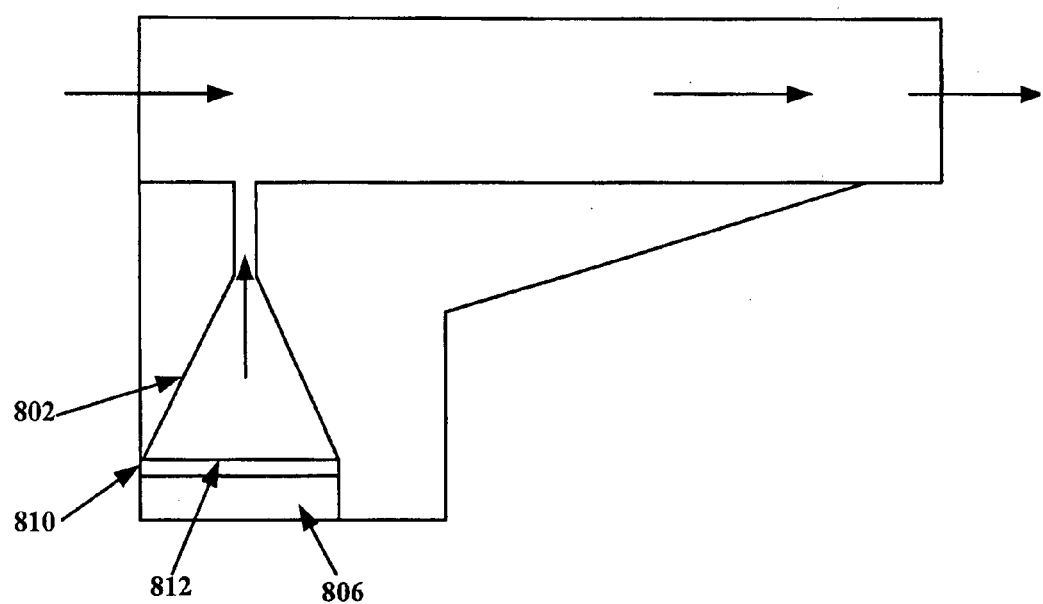
Figure 9:
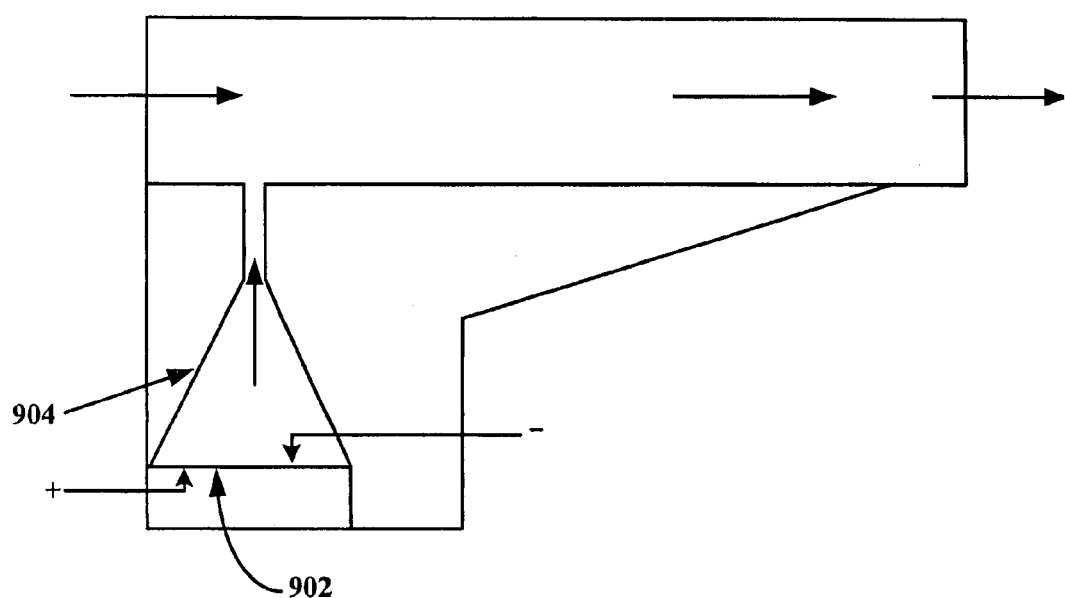
Figure 4:
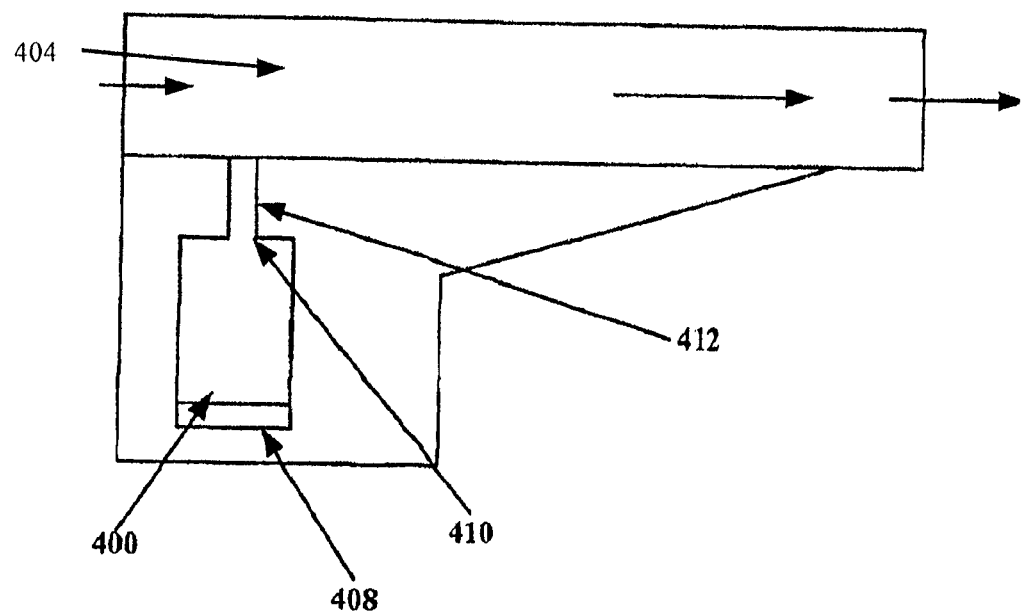
Figure 5:
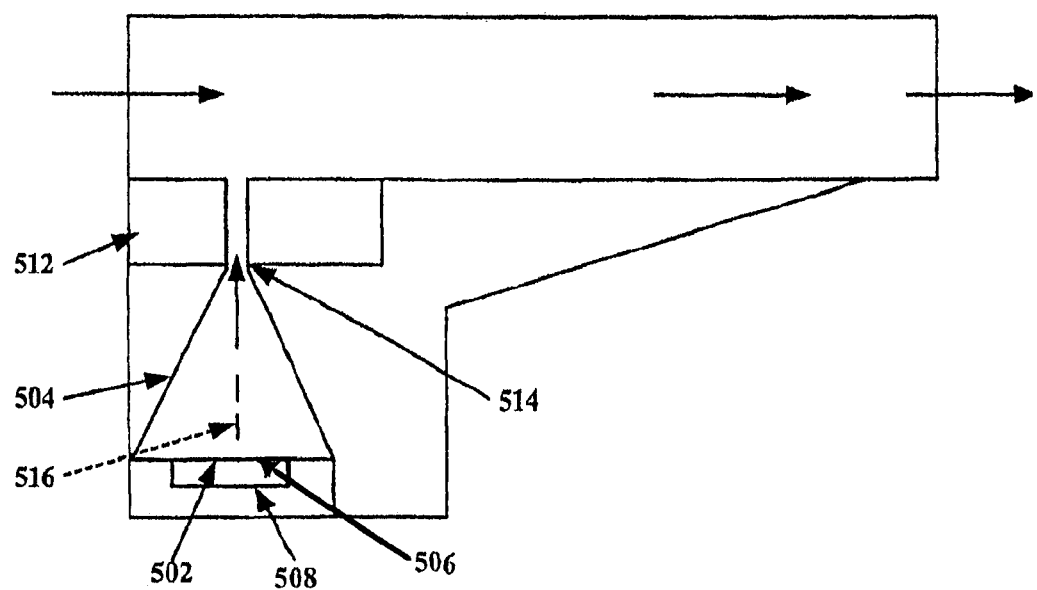
Figure 8:
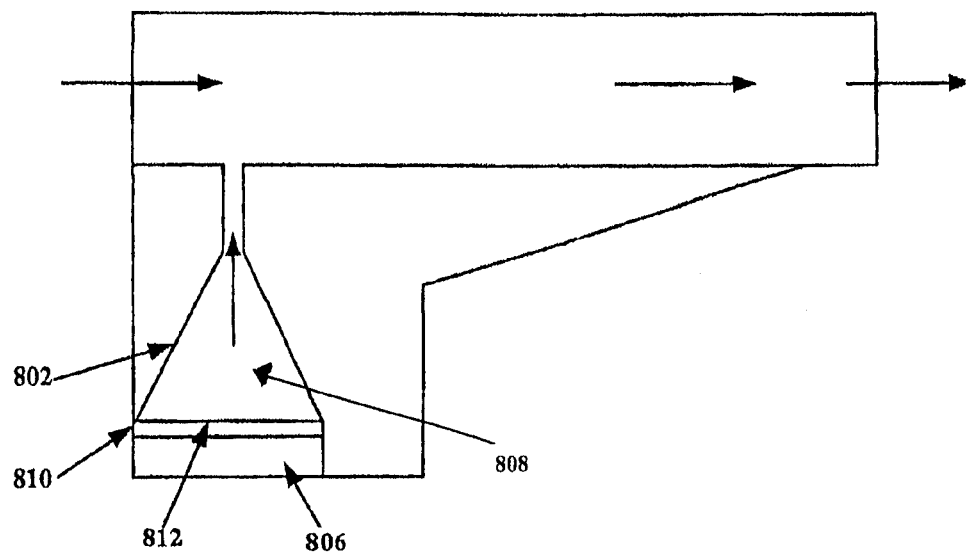

The sheets of drawings consisting of figures 4, 5 and 8 should be deleted to appear as per attached figures 4, 5 and 8.

Signed and Sealed this

Seventh Day of December, 2010

David J. Kappos
*Director of the United States Patent and Trademark Office*

CERTIFICATE OF CORRECTION (continued)
U.S. Pat. No. 7,318,434 B2

(12) United States Patent
Gumaste et al.

(10) Patent No.: US 7,318,434 B2
(45) Date of Patent: Jan. 15, 2008

(54) SYNTHETIC JET BASED MEDICAMENT DELIVERY METHOD AND APPARATUS

(75) Inventors: Anand V. Gumaste, West Windsor, NJ (US); John Bowers, Clarksburg, NJ (US)

(73) Assignee: Microdose Technologies, Inc., Monmouth Junction, NJ (US)

( * ) Notice: Subject to any disclaimer, the term of this patent is extended or adjusted under 35 U.S.C. 154(b) by 0 days.

(21) Appl. No.: 11/060,267

(22) Filed: Feb. 17, 2005

(65) Prior Publication Data
US 2005/0183724 A1    Aug. 25, 2005

Related U.S. Application Data
(60) Provisional application No. 60/547,323, filed on Feb. 24, 2004.

(51) Int. Cl.
*A61M 16/00*    (2006.01)
(52) U.S. Cl. ................. 128/203.15; 128/203.21
(58) Field of Classification Search ........ 128/200.14, 128/200.16, 203.15, 203.21
See application file for complete search history.

(56) References Cited
U.S. PATENT DOCUMENTS

| | | | |
|---|---|---|---|
| 2,517,482 A | 8/1950 | Hall | |
| 3,507,277 A | 4/1970 | Altounyan et al. | |
| 3,518,992 A | 7/1970 | Altounyan et al. | |
| 3,635,219 A | 1/1972 | Altounyan et al. | 128/266 |
| 3,653,380 A * | 4/1972 | Hansen | 128/203.15 |
| 3,795,244 A | 3/1974 | Lax et al. | 128/266 |
| 3,807,400 A | 4/1974 | Cocozza | 128/266 |
| 3,831,606 A | 8/1974 | Damani | 128/266 |
| 3,948,264 A * | 4/1976 | Wilke et al. | 128/203.15 |
| 4,240,418 A * | 12/1980 | Rosskamp et al. | 128/203.15 |
| 4,452,239 A * | 6/1984 | Malem | 128/200.17 |
| 5,260,321 A * | 11/1993 | Hof et al. | 514/338 |
| 5,349,947 A * | 9/1994 | Newhouse et al. | 128/203.21 |
| 5,429,302 A * | 7/1995 | Abbott | 239/102.2 |
| 5,458,135 A | 10/1995 | Patton et al. | 128/200.14 |
| 5,497,763 A * | 3/1996 | Lloyd et al. | 128/200.14 |
| 5,694,920 A * | 12/1997 | Abrams et al. | 128/200.16 |
| 5,699,649 A * | 12/1997 | Abrams et al. | 53/428 |
| 5,724,959 A * | 3/1998 | McAughey et al. | 128/203.15 |
| 5,740,793 A * | 4/1998 | Hodson et al. | 128/203.15 |
| 5,758,823 A | 6/1998 | Glezer et al. | 239/4 |
| 5,823,434 A * | 10/1998 | Cooper | 239/102.2 |
| 5,894,990 A | 4/1999 | Glezer et al. | 239/423 |
| 5,938,118 A * | 8/1999 | Cooper | 239/102.2 |
| 6,026,809 A | 2/2000 | Abrams et al. | 128/203.15 |
| 6,142,146 A | 11/2000 | Abrams et al. | 128/203.15 |
| 6,152,130 A * | 11/2000 | Abrams et al. | 128/204.21 |
| 6,328,033 B1 * | 12/2001 | Avrahami | 128/203.15 |

(Continued)

FOREIGN PATENT DOCUMENTS

WO    WO 97/26934    *    7/1997

(Continued)

*Primary Examiner*—Steven O. Douglas
(74) *Attorney, Agent, or Firm*—Hayes Soloway P.C.

(57) ABSTRACT

A dry powder inhaler consisting of first chamber having an orifice for holding a dry powder and a gas, and a second chamber for receiving a deaggregated form of the dry powder and for communicating the deaggregated dry powder to a user. A synthetic jet drives the dry powder from the first chamber to the second chamber.

40 Claims, 10 Drawing Sheets